United States Patent [19]
Vorbrüggen et al.

[11] Patent Number: 5,696,255
[45] Date of Patent: Dec. 9, 1997

[54] PROCESS FOR THE PRODUCTION OF 2-FLUOROPURINE DERIVATIVES

[75] Inventors: Helmut Vorbrüggen; Konrad Krolikiewicz, both of Berlin, Germany; Randolph C. Wirsching, Livermore; John G. Bauman, Alameda, both of Calif.

[73] Assignee: Schering Aktiengesellschaft, Berlin, Germany

[21] Appl. No.: 465,452

[22] Filed: Jun. 5, 1995

Related U.S. Application Data

[63] Continuation of Ser. No. 981,333, Nov. 25, 1992, abandoned.

[30] Foreign Application Priority Data

Nov. 25, 1991 [DE] Germany .......................... 41 39 238.8
Dec. 12, 1991 [DE] Germany .......................... 41 41 454.3

[51] Int. Cl.$^6$ .................. C07H 1/00; C07H 19/167; C07H 19/173
[52] U.S. Cl. ................ 536/55.3; 536/26.71; 536/27.3
[58] Field of Search ................ 536/55.3, 26.71, 536/27.3

[56] References Cited

U.S. PATENT DOCUMENTS 3,983,104 9/1976 Vorbrüggen .......................... 536/27.61
4,090,021 5/1978 Vorbrüggen .......................... 536/27.61

FOREIGN PATENT DOCUMENTS 24 41 484  3/1976  Germany.

OTHER PUBLICATIONS

Montgomery et al., J. Am. Chem. Soc., 82:463–468 (Jan. 20, 1960).

Montgomery et al., J. Med. Chem., 12:498–504 (May 1969).

Robins et al., Can. J. Chem., 59:2601–2607 (1981).

Robins et al., Can. J. Chem., 59:2608–2611 (1981).

Vorbrüggen et al., Liebigs Ann. Chem., pp. 745–761 (1976).

Montgomery et al., J. Org. Chem., 33:432–434 (1968).

Lopez, Letters in Chemical and Engineering News, p. 2 (Dec. 21, 1992).

*Primary Examiner*—Gary L. Kunz
*Attorney, Agent, or Firm*—Millen, White, Zelano, & Branigan, P.C.

[57] ABSTRACT

This invention relates to a process for the production of 2-fluoropurine derivatives from 2-aminopurine derivatives, which are reacted in HF/pyridine or HF/pyridine/$H_2O$ in the presence of a nitrite.

52 Claims, No Drawings

PROCESS FOR THE PRODUCTION OF 2-FLUOROPURINE DERIVATIVES

This is a continuation of the application Ser. No. 07/981,333 filed Nov. 25, 1992, now abandoned.

SUMMARY OF THE INVENTION

The invention relates to a new production of 2-fluoropurine nucleosides and their 5'-phosphates as well as their use for the production of pharmaceutical products.

According to treatises by J. Montgomery et al., free 2-aminoadenosine can be converted in a Schiemann reaction with aqueous fluoroboric acid to 2-fluoroadenosine (J. Montgomery and K. Hewson, J.A.C.S. 82, 463 (1960)). But, this process is unsuitable for preparative purposes, since the yields are under 10%.

It is further known in the literature that 2-aminoadenosine-2',3',5'-tri-O-acetate can be converted with tert-butyl nitrite or sodium nitrite in 50% HF/pyridine to a mixture of the corresponding 2-fluoroadenosine-2',3',5'-tri-O-acetate and 2,6-difluoro-nebularine-2',3',5'-tri-O-acetate, which, with dry ammonia gas in 1,2-dimethoxy-ethane, yields pure 2-fluoroadenosine-2',3',5'-tri-O-acetate in about a 60% yield (M. J. Robins, B. Uznanski, Can. J. Chem. 59, 2608 (1961)). A drawback of this process, however, is that because of the obtained mixture, another reaction step is necessary to obtain the pure 2-fluoronucleoside.

But, since 2-aminoadenosine cannot be selectively acetylated to 2-aminoadenosine-2',3',5'-tri-O-acetate (cf., i.a., J. A. Montgomery and K. Hewson, J. Med. Chem. 12, 498 (1969))—instead of the tri-O-acetate, a crystalline mixture of mainly adenosine-$N^2$-2',3',5'-O-tetraacetate in addition to a little pentaacetate is obtained—the 2-aminoadenosine-2',3',5'-tri-O-acetate necessary for the performance of the Schiemann reaction in 50% HF-pyridine according to M. J. Robins and B. Uznanski, Can. J. Chem. 59, 2608 (1981) is accessible only in a roundabout way and at great expense (M. J. Robins, B. Urbanski, Can. J. Chem. 59, 2601 (1981)).

In summary, it can be observed that in all known processes, the 2-fluorination is performed by using O-protected nucleosides or nucleotides or only leads to very small yields of process product.

It was therefore surprising that, in accordance with the present invention, unprotected compounds of formula II

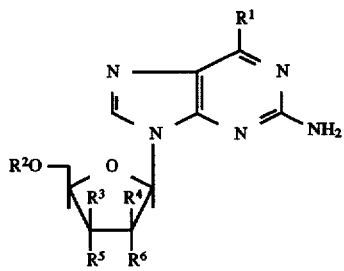

can be reacted in up to a 70% yield in, preferably 50%, HF/pyridine or, preferably 50%, HF/pyridine/$H_2O$ to the corresponding 2-fluoropurine derivatives of formula I

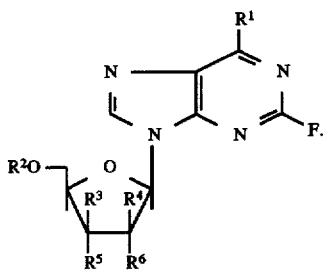

This invention therefore relates to a new process for the production of 2-fluoropurine derivatives of general formula I

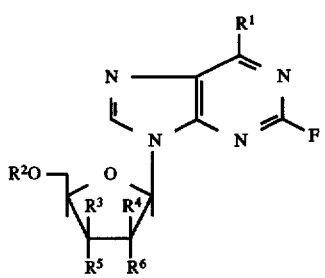

in which
$R^1$ is OH, $NH_2$, $NR^7R^8$ or $NR^9R^{10}$,
$R^2$ is hydrogen or

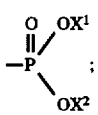

$X^1$ and $X^2$, independent of one another, are each hydrogen, Li, Na, K, or benzyl,
$R^3$, $R^4$, $R^5$ and $R^6$, independent of one another, are each hydrogen or OH,
$R^7$ and $R^8$, independent of one another, are each hydrogen, $C_1$–$C_4$ alkyl, $C_7$–$C_8$ aralkyl, a heterocyclic radical, $C_3$–$C_7$ cycloalkyl, or $R^7$ and $R^8$ together with the N atom can form a $C_4$–$C_7$ ring, which optionally contains 1–3 additional heteroatoms, or if $R^7$ is hydrogen, $R^8$ can also be OH or $NH_2$,
$R^9$ is hydrogen or $C_1$–$C_4$ alkyl,
$R^{10}$ is —$(CH_2)_n$—$R^{11}$,

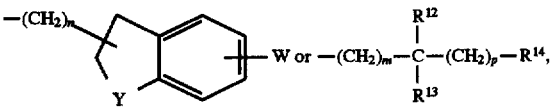

m, n and p, independent of one another, are each 0, 1 or 2,
$R^{11}$ is $C_3$–$C_7$ cycloalkyl, cyclohexenyl, bicycloheptyl or bicycloheptenyl, wherein $C_5$–$C_7$-cycloalkyl, cyclohexenyl, bicycloheptyl and bicycloheptenyl can be optionally substituted by $C_1$–$C_4$ alkyl,
Y is nitrogen, oxygen, sulfur, methylene, —$CH_2Z$— or —$ZCH_2$—, and Z is nitrogen, oxygen or sulfur,
$R^{12}$ and $R^{13}$, independent of one another, are each hydrogen, OH, phenyl or $C_1$–$C_4$ alkyl,
$R^{14}$ is hydrogen, OH, $C_1$–$C_4$ alkyl, unsubstituted phenyl or phenyl substituted by one to three of the following radicals, $C_1$–$C_4$ alkyl, $C_1$–$C_4$ alkoxy, OH, $C_1$–$C_4$ alkanoyloxy, benzyloxy, trifluoromethyl and/or halogen, W is hydrogen, $C_1$–$C_4$ alkoxy, $C_1$–$C_4$ alkylthio, halogen or $C_1$–$C_4$ alkyl optionally substituted by OH, $C_1$–$C_4$ alkoxy, CN, $COOR^{15}$ or $CONHR^{16}$, $R^{15}$ is hydrogen or $C_1$–$C_4$ alkyl, $R^{16}$ is hydrogen or $C_1$–$C_4$ alkyl, characterized in that a 2-aminopurine derivative of general formula II

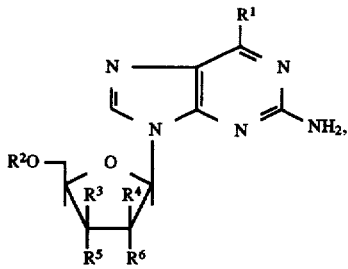

in which $R^1$, $R^2$, $R^3$, $R^4$, $R^5$ and $R^6$ have the above-indicated meanings, is reacted in HF/pyridine or HF/pyridine/$H_2O$ in the presence of a nitrite of general formula III,

in which $R^{17}$ preferably is tert-butyl, Li, Na or K; and optionally, if $R^2$ is hydrogen, is later converted to the phosphate.

The compounds of formula II are "unprotected" in that 2',3' and/or 5' hydroxy groups are not protected.

Of radicals $R^3$, $R^4$, $R^5$, $R^6$, preferably at least two radicals are hydrogen and at most two radicals are hydroxy, and two hydroxy radicals must never be on the same carbon atom.

The alkyl radicals in $R^7$, $R^8$, $R^9$, $R^{12}$, $R^{13}$, $R^{14}$, $R^{15}$ and $R^{16}$ can be methyl, ethyl, propyl, isopropyl, butyl, isobutyl, sec-butyl and tert-butyl.

Suitable alkyl radicals for W include, for example, unsubstituted radicals such as methyl, ethyl, propyl, isopropyl, butyl, isobutyl, sec-butyl and tert-butyl, as well as $C_1$–$C_4$-alkyl radicals, substituted by hydroxy, $C_1$–$C_4$-alkoxy, CN, $COOR^{15}$ or $CONHR^{16}$, such as, for example, hydroxymethyl, hydroxyethyl, hydroxypropyl, hydroxybutyl, methoxymethyl, methoxyethyl, methoxypropyl, methoxybutyl, ethoxymethyl, ethoxyethyl, ethoxypropyl, ethoxybutyl, cyanomethyl, cyanoethyl, cyanopropyl, cyanobutyl, carboxymethyl, carboxyethyl, carboxypropyl, carboxybutyl, methoxycarbonylmethyl, ethoxycarbonylmethyl, methoxycarbonylethyl, ethoxycarbonylethyl, carbamoyl, carbamoylmethyl, carbamoylethyl, carbamoylpropyl, carbamoylbutyl, N-methylcarbamoylmethyl, N-methylcarbamoylethyl.

Suitable aralkyl radicals for $R^7$ and $R^8$ are benzyl, phenethyl and 1-phenylethyl.

Heterocyclic radicals for $R^7$ and $R^8$ contain 5–10 ring atoms with 1–3 N, O and/or S hetero ring atoms.

Suitable heterocyclic radicals for $R^7$ and $R^8$ include 2-pyridyl, 3-pyridyl, 4-pyridyl, 2-furyl, 3-furyl, 2-thienyl, 3-thienyl, 2-pyrrolyl, 3-pyrrolyl, 2-indolyl and 3-indolyl, which optionally can be substituted by fluorine, chlorine, bromine, cyano, hydroxy, carboxy, $C_1$–$C_4$ alkoxy or $C_1$–$C_4$ alkyl.

Cycloalkyl radicals for $R^7$ and $R^8$ are cyclopropyl, cyclobutyl, cyclopentyl, cyclohexyl and cycloheptyl, and cyclopentyl, cyclohexyl and cycloheptyl can be substituted by cyano, hydroxy, methyl, ethyl, propyl, butyl, methoxy, ethoxy, carboxy, methoxycarbonyl or ethoxycarbonyl.

Cycloalkyl radicals for $R^{11}$ are cyclopropyl, cyclobutyl, cyclopentyl, cyclohexyl and cycloheptyl, and cyclopentyl, cyclohexyl and cycloheptyl can be substituted by methyl, ethyl, propyl, isopropyl, butyl, isobutyl, sec-butyl or tert-butyl.

The cyclohexenyl group for $R^{11}$ can optionally be substituted by methyl, ethyl, propyl, isopropyl, butyl, isobutyl, sec-butyl or tert-butyl.

The bicycloheptyl group for $R^{11}$ is preferably [2.2.1]-bicycloheptyl. The latter can optionally be substituted by methyl, ethyl, propyl, isopropyl, butyl, isobutyl, sec-butyl or tert-butyl.

The bicycloheptenyl radical for $R^{11}$ is preferably [2.2.1] bicycloheptenyl, which can optionally be substituted by methyl, ethyl, propyl, isopropyl, butyl, isobutyl, sec-butyl or tert-butyl.

If $R^7$ and $R^8$ together represent a $C_4$–$C_7$ ring, radicals such as, for example, pyrrolidine, piperidine or morpholine are preferred.

As substituted phenyl radicals for $R^{14}$, methylphenyl, ethylphenyl, propylphenyl, butylphenyl, dimethylphenyl, methoxyphenyl, ethoxyphenyl, hydroxyphenyl, dihydroxyphenyl, formyloxyphenyl, acetyloxyphenyl, propionyloxyphenyl, butyryloxyphenyl, benzyloxyphenyl, trifluoromethylphenyl, fluorophenyl, chlorophenyl, bromophenyl, difluorophenyl, dichlorophenyl, dibromophenyl are suitable.

The alkoxy radical for W can be methoxy, ethoxy, propoxy or butoxy.

The alkylthio radical for W can be methylthio, ethylthio, propylthio or butylthio.

For halogen, fluorine, chlorine and bromine are suitable.

The object of the invention is consequently the reaction of compounds of general formula II in, preferably 50%, HF/pyridine or, preferably 50%, HF/pyridine/$H_2O$ in the presence of, preferably, tert-butyl nitrite or sodium nitrite at temperatures of –50°–+25° C., preferably at temperatures of –30°—10° C., to obtain compounds of general formula I.

The $H_2O$ content of the reaction mixture is preferably 0–10%. The HF content, based on the total amount of HF and pyridine, is 10–16% HF, preferably 40–60% HF.

The necessary starting materials of general formula II for the production of the 2-fluoropurine derivatives of general formula I can be produced according to H. Vorbrueggen and K. Krolikiewicz, Liebigs Annalen [Liebig Annals] 745 (1976) or DOS 2,441,484 (corresponding to U.S. Pat. No. 3,983,104 and U.S. Pat. No. 4,090,021).

If necessary, the functional groups in $R^1$ can be protected according to the methods known to one skilled in the art.

The 5'-phosphates can be used as free phosphoric acids as well as salts, in particular as sodium salts, or as benzyl esters.

When benzyl esters are used, they can be cleaved again after the 2-fluorination according to methods known to one skilled in the art.

Working up of the HF/pyridine reaction solution takes place suitably with a suspension of excess finely powdered $CaCO_3$ in ice water with vigorous stirring and filtration of the resultant calcium fluoride. Further, excess hexamethyldisiloxane can be added to the crude reaction mixture with vigorous stirring, so that the phases are at least somewhat mixed, and the volatile trimethylsilyl fluoride (boiling point 17° C.) and water format temperatures between –20° C. and 24° C. The trimethylsilyl fluoride can be cleaved in a receiver with alkaline solution to form alkali fluorides and hexamethyldisiloxane. The working up with hexamethyldisiloxane is particularly suitable for the reaction of the 5'-phosphates.

After the 2-fluorination, if introduced in advance, the protecting groups of the functional groups in $R^1$ are again cleaved according to the methods known to one skilled in the art.

In compounds of general formula I wherein $R^2$ is H, the phosphate group can be introduced after the 2-fluorination according to methods known to one skilled in the art.

The 2-fluoroadenosine and its $N^6$-substituted analogs according to formula I are valuable intermediate products for the production of new therapeutically important nucleosides and nucleotides.

Thus, by protection of the 3',5'-alcoholic hydroxyl groups in the compounds of formula I ($R^2$=H), e.g., with 1,3-dichloro-1,1,3,3-tetraisopropyl-disiloxane in pyridine, the protected derivatives are obtained, in which the 2'-hydroxyl group can be converted selectively to the triflate, nonaflate, mesylate or tosylate. Subsequent Walden inversion by reaction with alkali salts, amine salts or tetraalkylammonium salts, e.g., of acetic acid or benzoic acid, yields the protected ara (arabinofuranosyl) derivatives. After cleavage of the protecting groups, for example, the thus obtained ara-2-fluoroadenosine can be phosphorylated selectively in the 5'-position to a leukemia therapeutic agent known as ara-2-fluoroadenosine-5'-phosphate (FLUDARA®; fludarabine phosphate). See also related U.S. Pat. No. 5,602,246.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications cited above, and of corresponding German applications P 41 39 238.8 and P 41 41 454.3, are hereby incorporated by reference.

REAGENTS

1) Production of 50% HF in pyridine 2 ml of abs. pyridine is slowly instilled in 5 ml of 70% HF in pyridine (Aldrich) at −60° C. and heated to −30° C.

2) Thin-layer chromatography

For the thin-layer chromatography, HPTLC-nano-silica gel slabs no. 5628 of the Merck Company (Darmstadt) are used.

3) Silica gel for the column chromatography

For the column chromatography, silica gel no. 10757, which contains 40% $H_2O$, of the Merck Company (Darmstadt) is used.

EXAMPLES

Example 1

2-Fluoroadenosine 1.13 g (4 mmol) of finely powdered 2-aminoadenosine is suspended in 7 ml of 50% HF in pyridine at −30° C. with vigorous stirring and then 1.03 g of 90% tert-butyl nitrite (≈9 mmol) is slowly added within 15 minutes with the help of a syringe. A light gas generation takes place and the suspended 2-aminoadenosine goes into solution with yellow coloring of the reaction mixture. After 30 minutes of stirring at −20° C.→−25° C., only traces of 2-aminoadenosine ($R_f$=0.4) as well as some isoguanosine ($R_f$=0.25) can be detected by thin-layer chromatography (upper phase of n-butanol-acetic acid-$H_2O$=4:1:5) in addition to the newly resulting 2-fluoroadenosine ($R_f$=0.57). The reaction mixture is instilled in an ice-cold suspension of 50 g (0.5 mol) of calcium carbonate with vigorous stirring under $CO_2$ generation and the suspension is then stirred for 30 minutes at 0° C. The undissolved precipitate of calcium carbonate and calcium fluoride is then filtered on a layer of about 20 g of Celite and rewashed with 150 ml of a mixture of pyridine-$H_2O$ (1:9). After evaporation of the light yellow filtrate, at a 10 mm vacuum, the partially crystalline residue (1.3 g) is suspended in 30 ml of methanol-$H_2O$ (1:1) at 40° C., and small amounts remain undissolved, mixed with 10 g of silica gel (40% $H_2O$) and concentrated by evaporation at a 10 mm vacuum.

After feeding the dry silica gel containing the substance on a column of 15 g of silica gel (40% $H_2O$), which was taken up with the upper phase of the mixture of ethyl acetate-methyl glycol-$H_2O$=4:1:2, the elution with this mixture in the first 100 ml produces only traces of substance, which are discarded, while the next 300 ml of eluate produces 0.760 g (66.7%) of pure 2-fluoroadenosine, which crystallizes during heating with 5 ml of $H_2O$ on the water bath, melting point 237°–242° C. Further elution with 50 ml yields 18 mg more of slightly contaminated 2-fluoroadenosine.

Example 2

Production of 2-fluoroadenosine

As described in example 1, 1.13 g (4 mmol) of finely powdered 2-aminoadenosine is suspended at −25° C. in 7 ml of 50% HF in pyridine and 0.55 g (8 mmol) of sodium nitrite is added in portions with stirring within 15 minutes at −25° C. After 1 hour at −25° C., it is worked up with $CaCO_3$ as described in example 1, and 1.4 g of crude product is obtained, which, with chromatography on silica gel, yields 0.708 g (62.1%) of pure, homogeneous 2-fluoroadenosine.

Example 3

Production of 2-fluoroadenosine 0.282 g (1 mmol) of 2-aminoadenosine is suspended in a mixture of 7 ml of 50% HF-pyridine and 0.35 ml of $H_2O$ at −30° C. and within 30 minutes, 1.2 ml (~9 mol) of tert-butyl nitrite is instilled slowly with vigorous stirring at −30° C. After another 30 minutes at −25°→−30° C., the reaction mixture is instilled slowly in 120 ml of 33% aqueous ammonia at −10° C. with stirring and stirred for 1 hour at 0° C. After adding 7 g of solid calcium hydroxide, it is stirred for another 15 minutes at 0° C., filtered and washed with 40 ml of $H_2O$. The light yellow filtrate is carefully concentrated by evaporation at about 25° C.–30° C. to about 15 ml and $CO_2$ is introduced. After filtering off the small amount of precipitate and after washing the precipitate with 10 ml of $H_2O$, the filtrate is concentrated by evaporation at a 10 mm vacuum. The yellowish-brown residue (0.39 g) is dissolved in 15 ml of methanol-$H_2O$ (1:1), mixed with 10 g of silica gel (40% $H_2O$) and evaporated at a 10 mm vacuum. After feeding dry silica gel containing the substance on a column of 15 g of silica gel (40% $H_2O$), which was taken up with isopropanol, elution with about 300 ml of isopropanol yields 0.261 g (~91%) of crude 2-fluoroadenosine, which still contains a little 2-aminoadenosine as well as isoguanosine.

Example 4

2-Fluoro-$N^6$,$N^6$-pentamethyleneadenosine [2-Fluoro-6-piperidino-adenosine]

As described in example 1, 0.7 g (2 mmol) of finely powdered 2-amino-$N^6$,$N^6$-pentanemethyleneadenosine (2-amino-6-piperidino-adenosine) is dissolved at −25° C. in 7 ml of 50% HF-pyridine and 0.412 g (2 mmol) of tert-butyl nitrite is added within 5 minutes with stirring. After 3 minutes at −25° C., it is worked up, as indicated under example 1, and the Celite-CaCO$_3$-CaF$_2$ layer is rewashed with 150 ml of methanol-H$_2$O (1:1). Evaporation of the filtrate yields 0.89 g of crude product which is dissolved in 20 ml of methanol and mixed with 15 g of silica gel and concentrated by evaporation. This dry 15 g of silica gel containing the substance is put on a column of another 15 g of silica gel, which contains 40% H$_2$O and is generated with the upper phase of ethyl acetate-methyl glycol-H$_2$O (4:1:2). After a first running of 25 ml, the further 125 ml of eluate yields 0.64 (90%) of light yellow crystalline 2-fluoro-N$^6$, N$^6$-pentamethyleneadenosine, which, in the recrystallization from ethyl acetate, yields colorless, analytically pure product, melting point 164° C.

Example 5

Production of 2-fluorinosine 0.566 g (2 mmol) of guanosine dihydrate is dissolved in 7 ml of HF/pyridine, as described in example 1, and mixed at −25° C. with 0.412 g (2 mmol) of tert-butyl nitrite within 5 minutes, and then stirred for another 30 minutes at −30° C., worked up and the Celite-CaCO$_3$-CaF$_2$ layer is rewashed with 150 ml of methanol-H$_2$O (1:1). After evaporating the filtrate, dissolving the residue (0.9 g) in 10 ml of H$_2$O, adding 15 g of silica gel and evaporating from the rotary evaporator, dry silica gel containing the substance is obtained. After feeding the dry silica gel to a column, produced with the upper phase of n-butanol-acetic acid-H$_2$O (4:1:5), of another 15 g of silica gel, which contains 40% H$_2$O, the first 150 ml of eluate yields 0.52 g (90.9%) of colorless, crystalline 2-fluorinosine.

Example 6

10 g (35.43 mmol) of 2-aminoadenosine is mixed in a 250 ml polyethylene flask at −5° C. with 50 ml of 56% HF-pyridine solution and the suspension is slowly heated with stirring to 12° C., resulting in clear solution then is cooled to −16° C. internal temperature and a solution of 3.4 g (40 mmol) of KNO$_2$ in 2 ml of water is instilled with stirring within 20 minutes at −16 to −7° C. internal temperature. After further 30 minutes of stirring at −7 to −10° C., the reaction mixture is kept for 3 hours more at +30° C., is cooled to −35° C. and within 40 minutes is slowly and carefully diluted with 41.5 ml of absolute pyridine, and a fine, greasy precipitate precipitates. Then, 50.2 ml of acetic anhydride is carefully instilled within 30 minutes at −5° C. to +12° C., and CH$_3$COF escapes with foaming. After approximately 4 hours at +18° C. to +22° C., the reaction mixture is slowly added to a solution of 30.92 g (0.5 mol) of boric acid in 600 ml of H$_2$O, is stirred for 30 minutes more and filtered.

The crystals are washed in portions with 80 ml of H$_2$O and 80 ml of methanol. The lightly colored crystals after drying in a vacuum at +60° C., yield 10.5 g of 2-fluoroadenosine-2',3',5'-tri-O-acetate of a melting point of 201.9° C.

After concentration by evaporation of the filtrate to 400 ml and repeated extraction with a total of 1 liter of ethyl acetate, the ethyl acetate solution is washed with NaHCO$_3$ and NaCl solution, dried on Na$_2$SO$_4$ and concentrated by evaporation, and 1.5 g of partially crystalline residue is obtained (crude yield 12 g=83.3%).

Recrystallization from ethyl acetate-ethanol (4:1) yields 10.61 g (72.8%) of pure 2-fluoroadenosine-2',3',5'-tri-O-acetate of a melting point of 203.9° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirits and scope thereof, can make various changes and modifications of the invention to adapt it to various usages and conditions.

What is claimed is:

1. A process for production of a 2-fluoropurine compound of formula I

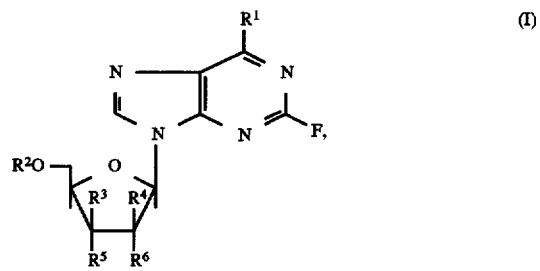

wherein

R$^1$ is OH, NH$_2$, NR$^7$R$^8$ or NR$^9$R$^{10}$;

R$^2$ is hydrogen or

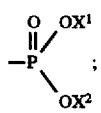

X$^1$ and X$^2$, independent of one another, are each H, Li, Na or K;

R$^3$, R$^4$, R$^5$ and R$^6$, independent of one another, are each H or OH, and R$^3$ and R$^5$ are not simultaneously both OH and R$^4$ and R$^6$ are not simultaneously both OH;

R$^7$ and R$^8$, independent of one another, are each H, C$_1$–C$_4$-alkyl, C$_7$–C$_8$-aralkyl, an unsubstituted heterocyclic radical, a heterocyclic radical substituted by F, Cl, Br, CN, OH, COOH, C$_1$–C$_4$-alkoxy or C$_1$–C$_4$-alkyl, unsubstituted C$_3$–C$_7$-cycloalkyl, C$_5$–C$_7$-cycloalkyl substituted by CN, OH, C$_1$–C$_4$-alkyl, methoxy, ethoxy, COOH, methoxycarbonyl, or ethoxycarbonyl, or R$^7$ and R$^8$ together with the N atom can form a C$_4$–C$_7$ ring, which optionally contains 1–3 additional heteroatoms, or, if R$^7$ is H, R$^8$ can also be OH or NH$_2$;

R$^9$ is H or C$_1$–C$_4$-alkyl;

R$^{10}$ is —(CH$_2$)$_n$—R$^{11}$,

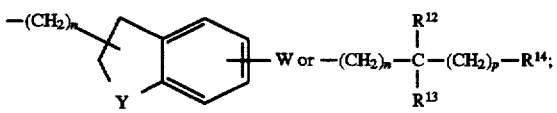

m, n and p, independent of one another, are each 0, 1 or 2;

R$^{11}$ is unsubstituted C$_3$–C$_7$-cycloalkyl, unsubstituted cyclohexenyl, unsubstituted bicycloheptyl, unsubstituted bicycloheptenyl, C$_5$–C$_7$-cycloalkyl substituted by C$_1$–C$_4$-alkyl, cyclohexenyl substituted by C$_1$–C$_4$-alkyl, bicycloheptyl substituted by $C_1$–$C_4$-alkyl or bicycloheptenyl substituted by $C_1$–$C_4$-alkyl;

Y is nitrogen, oxygen, sulfur, methylene, —$CH_2Z$— or —$ZCH_2$—; and

Z is nitrogen, oxygen or sulfur;

$R^{12}$ and $R^{13}$, independent of one another, are each H, OH, phenyl or $C_1$–$C_4$-alkyl;

$R^{14}$ is H, OH, $C_1$–$C_4$-alkyl, unsubstituted phenyl or phenyl substituted by one to three substituents, each substituent being selected from the following: $C_1$–$C_4$-alkyl, $C_1$–$C_4$-alkoxy, OH, $C_1$–$C_4$-alkanoyloxy, benzyloxy, trifluoromethyl and halogen;

W is H, $C_1$–$C_4$-alkoxy, $C_1$–$C_4$-alkylthio, halogen, $C_1$–$C_4$-alkyl, or $C_1$–$C_4$-alkyl substituted by OH, $C_1$–$C_4$-alkoxy, CN, $COOR^{15}$ or $CONHR^{16}$;

$R^{15}$ is H or $C_1$–$C_4$-alkyl; and $R^{16}$ is H or $C_1$–$C_4$-alkyl;

wherein $R^1$ is optionally protected by a protecting group; comprising directly reacting a 2-aminopurine compound of formula II

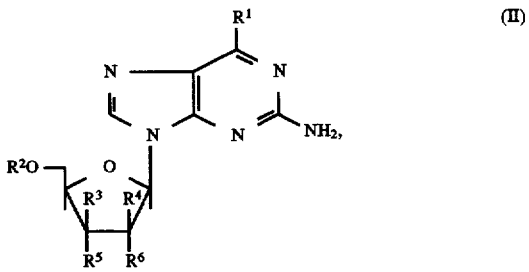

(II)

wherein $R^1$, $R^2$, $R^3$, $R^4$, $R^5$ and $R^6$ have the meanings indicated above, in HF/pyridine or HF/pyridine/$H_2O$ in the presence of a nitrite of formula III,

$R^{17}ONO$    (III), wherein $R^{17}$ is tert-butyl, Li, Na or K;

optionally, if $R^2$ is hydrogen, converting $R^2$ to form 5'-phosphate; and optionally, if $R^1$ is protected, cleaving said protecting group.

2. A process according to claim 1, wherein $R^7$ and $R^8$ are each H.

3. A process according to claim 1, wherein $R^7$ and $R^8$ are each H, $C_1$–$C_4$-alkyl, $C_7$–$C_8$-aralkyl, unsubstituted $C_3$–$C_7$-cycloalkyl or $C_5$–$C_7$-cycloalkyl substituted by CN, OH, $C_1$–$C_4$-alkyl, methoxy, ethoxy, COOH, methoxycarbonyl or ethoxycarbonyl.

4. A process according to claim 1, wherein $R^7$ and $R^8$ are each H, $C_1$–$C_4$-alkyl, $C_7$–$C_8$-aralkyl, unsubstituted $C_3$–$C_7$-cycloalkyl or $C_5$–$C_7$-cycloalkyl substituted by CN, OH, $C_1$–$C_4$-alkyl, methoxy, ethoxy, COOH, methoxycarbonyl or ethoxycarbonyl, 2-pyridyl, 3-pyridyl, 4-pyridyl, 2-furyl, 3-furyl, 2-thienyl, 3-thienyl, 2-pyrrolyl, 3-pyrrolyl, 2-indolyl or 3-indolyl, or $R^7$ and $R^8$ together with the N atom are pyrrolidine, piperidine or morpholine.

5. A process according to claim 1, wherein $R^7$ and $R^8$, independent of one another, are each H, $C_1$–$C_4$-alkyl, $C_7$–$C_8$-aralkyl, an unsubstituted heterocyclic radical containing 5–10 ring atoms with 1–3 hetero ring atoms each selected from N, O and S atoms, a heterocyclic radical containing 5–10 ring atoms with 1–3 hetero ring atoms each selected from N, O and S atoms substituted by F, Cl, Br, CN, OH, COOH, $C_1$–$C_4$-alkoxy, $C_1$–$C_4$-alkyl, unsubstituted $C_3$–$C_7$-cycloalkyl, $C_5$–$C_7$-cycloalkyl substituted by CN, OH, $C_1$–$C_4$-alkyl, methoxy, ethoxy, COOH, methoxycarbonyl, or ethoxycarbonyl, or $R^7$ and $R^8$ together with the N atom can form a $C_4$–$C_7$ ring, which optionally contains 1–3 hetero ring atoms each selected from N and O atoms, or, if $R^7$ is H, $R^8$ can also be OH or $NH_2$.

6. A process according to claim 5, wherein said compound of formula II is reacted in HF/pyridine/$H_2O$ containing up to 10% $H_2O$.

7. A process according to claim 5, wherein the reaction of a compound of formula II is conducted at −50° C.–+25° C.

8. A process according to claim 5, wherein said nitrite of formula III is tert-butylnitrite or sodium nitrite.

9. A process according to claim 5, wherein said compound of formula II is 2-aminoadenosine.

10. A process according to claim 5, wherein said compound of formula II is 2-amino-6-piperidino-adenosine.

11. A process according to claim 5, wherein said compound of formula I is 2-fluoroadenosine, 2-fluoro-6-piperidino-adenosine or 2-fluorinosine.

12. A process according to claim 5, wherein $R^2$ is H.

13. A process according to claim 5, wherein $X^1$ and $X^2$ are each H.

14. A process according to claim 1, wherein $R^7$ and $R^8$ are each, independently, selected from the group consisting of $C_1$–$C_4$-alkyl, benzyl, phenethyl, 1-phenylethyl, 2-pyridyl, 3-pyridyl, 4-pyridyl, 2-furyl, 3-furyl, 2-thienyl, 3-thienyl, 2-pyrrolyl, 3-pyrrolyl, 2-indolyl, 3-indolyl, cyclopropyl, cyclobutyl, cyclopentyl, cyclohexyl or cycloheptyl.

15. A process according to claim 1, wherein $R^7$ and $R^8$ together are pyrrolidine, piperidine or morpholine.

16. A process according to claim 5, wherein two of the groups $R^3$, $R^4$, $R^5$ and $R^6$ are OH and the remaining two groups are H.

17. A process according to claim 16, wherein $R^5$ and $R^6$ are OH.

18. A process according to claim 16, wherein $R^5$ and $R^4$ are OH.

19. A process according to claim 5, wherein said compound of formula II is reacted in HF/pyridine.

20. A process according to claim 19, wherein said HF/pyridine contains 10–60% HF.

21. A process according to claim 19, wherein said compound of formula II is reacted in 40–60% HF/pyridine.

22. A process according to claims 19, further comprising instilling the HF/pyridine reaction mixture in a suspension of calcium carbonate and ice water followed by removal of undissolved precipitate by filtration and evaporation of the resultant filtrate.

23. A process according to claim 5, wherein $R^{17}$ is Li, Na or K.

24. A process according to claim 23, wherein $R^{17}$ is K.

25. A process according to claim 23, wherein $R^{17}$ is Na.

26. A process for production of a 2-fluoropurine compound of formula I

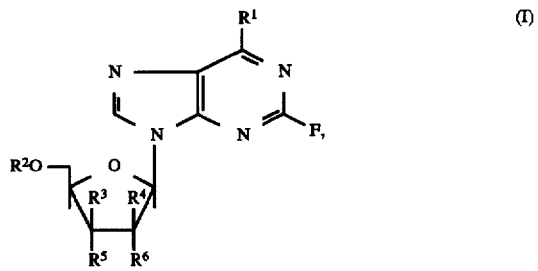

(I)

wherein $R^1$ is OH, $NH_2$, $NR^7R^8$ or $NR^9R^{10}$;

$R^2$ is hydrogen or

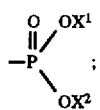

$X^1$ and $X^2$, independent of one another, are each H, Li, Na or K;

$R^3$, $R^4$, $R^5$ and $R^6$, independent of one another, are each H or OH, and $R^3$ and $R^5$ are not simultaneously both OH and $R^4$ and $R^6$ are not simultaneously both OH;

$R^7$ and $R^8$, independent of one another, are each H, $C_1$–$C_4$-alkyl, $C_7$–$C_8$-aralkyl, an unsubstituted heterocyclic radical, a heterocyclic radical substituted by F, Cl, Br, CN, OH, COOH, $C_1$–$C_4$-alkoxy or $C_1$–$C_4$-alkyl, unsubstituted $C_3$–$C_7$-cycloalkyl, $C_5$–$C_7$-cycloalkyl substituted by CN, OH, $C_1$–$C_4$-alkyl, methoxy, ethoxy, COOH, methoxycarbonyl, or ethoxycarbonyl, or $R^7$ and $R^8$ together with the N atom can form a $C_4$–$C_7$ ring, which optionally contains 1–3 additional heteroatoms, or, if $R^7$ is H, $R^8$ can also be OH or $NH_2$;

$R^9$ is H or $C_1$–$C_4$-alkyl;

$R^{10}$ is —$(CH_2)_n$—$R^{11}$,

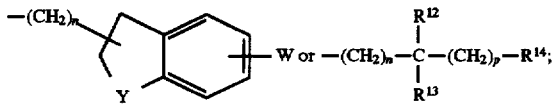

m, n and p, independent of one another, are each 0, 1 or 2;

$R^{11}$ is unsubstituted $C_3$–$C_7$-cycloalkyl, unsubstituted cyclohexenyl, unsubstituted bicycloheptyl, unsubstituted bicycloheptenyl, $C_5$–$C_7$-cycloalkyl substituted by $C_1$–$C_4$-alkyl, cyclohexenyl substituted by $C_1$–$C_4$-alkyl, bicycloheptyl substituted by $C_1$–$C_4$-alkyl or bicycloheptenyl substituted by $C_1$–$C_4$alkyl;

Y is nitrogen, oxygen, sulfur, methylene, —$CH_2Z$— or —$ZCH_2$—; and

Z is nitrogen, oxygen or sulfur;

$R^{12}$ and $R^{13}$, independent of one another, are each H, OH, phenyl or $C_1$–$C_4$-alkyl;

$R^{14}$ is H, OH, $C_1$–$C_4$-alkyl, unsubstituted phenyl or phenyl substituted by one to three substituents, each substituent being selected from the following: $C_1$–$C_4$-alkyl, $C_1$–$C_4$-alkoxy, OH, $C_1$–$C_4$-alkanoyloxy, benzyloxy, trifluoromethyl and halogen;

W is H, $C_1$–$C_4$-alkoxy, $C_1$–$C_4$-alkylthio, halogen, $C_1$–$C_4$-alkyl, or $C_1$–$C_4$-alkyl substituted by OH, $C_1$–$C_4$-alkoxy, CN, $COOR^{15}$ or $CONHR^{16}$;

$R^{15}$ is H or $C_1$–$C_4$-alkyl; and $R^{16}$ is H or $C_1$–$C_4$-alkyl;

wherein $R^1$ is optionally protected by a protecting group; consisting of directly reacting a 2-aminopurine compound of formula II

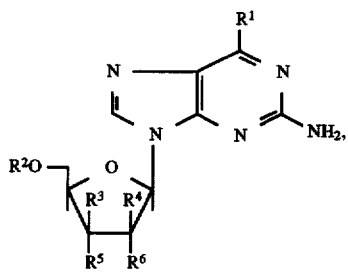

wherein $R^1$, $R^2$, $R^3$, $R^4$, $R^5$ and $R^6$ have the meanings indicated above, in HF/pyridine or HF/pyridine/$H_2O$ in the presence of a nitrite of formula III, $$R^{17}ONO \qquad (III),$$

wherein $R^{17}$ is tert-butyl, Li, Na or K;

optionally, if $R^2$ is hydrogen, converting $R^2$ to form 5'-phosphate; and optionally, if $R^1$ is protected, cleaving said protecting group.

27. A process for production of a 2-fluoropurine compound of formula I

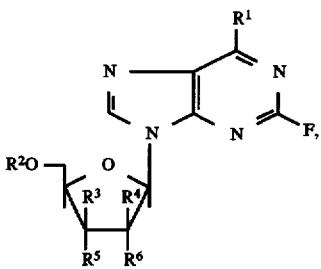

wherein $R^1$ is OH, $NH_2$, $NR^7R^8$ or $NR^9R^{10}$;

$R^2$ is hydrogen or

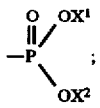

$X^1$ and $X^2$, independent of one another, are each H, Li, Na or K;

$R^3$, $R^4$, $R^5$ and $R^6$, independent of one another, are each H or OH, and $R^3$ and $R^5$ are not simultaneously both OH and $R^4$ and $R^6$ are not simultaneously both OH;

$R^7$ and $R^8$, independent of one another, are each H, $C_1$–$C_4$-alkyl, $C_7$–$C_8$-aralkyl, an unsubstituted heterocyclic radical, a heterocyclic radical substituted by F, Cl, Br, CN, OH, COOH, $C_1$–$C_4$-alkoxy or $C_1$–$C_4$-alkyl, unsubstituted $C_3$–$C_7$-cycloalkyl, $C_5$–$C_7$-cycloalkyl substituted by CN, OH, $C_1$–$C_4$-alkyl, methoxy, ethoxy, COOH, methoxycarbonyl, or ethoxycarbonyl, or $R^7$ and $R^8$ together with the N atom can form a $C_4$–$C_7$ ring, which optionally contains 1–3 additional heteroatoms, or, if $R^7$ is H, $R^8$ can also be OH or $NH_2$;

$R^9$ is H or $C_1$–$C_4$-alkyl;

$R^{10}$ is —$(CH_2)_n$—$R^{11}$,

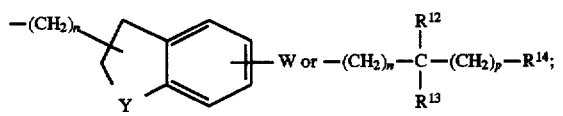

m, n and p, independent of one another, are each 0, 1 or 2;

$R^{11}$ is unsubstituted $C_3$–$C_7$-cycloalkyl, unsubstituted cyclohexenyl, unsubstituted bicycloheptyl, unsubstituted bicycloheptenyl, $C_5$–$C_7$-cycloalkyl substituted by $C_1$–$C_4$-alkyl, cyclohexenyl substituted by $C_1$–$C_4$-alkyl, bicycloheptyl substituted by $C_1$–$C_4$-alkyl or bicycloheptenyl substituted by $C_1$–$C_4$-alkyl;

Y is nitrogen, oxygen, sulfur, methylene, —$CH_2Z$— or —$ZCH_2$—; and

Z is nitrogen, oxygen or sulfur;

$R^{12}$ and $R^{13}$, independent of one another, are each H, OH, phenyl or $C_1$–$C_4$-alkyl;

$R^{14}$ is H, OH, $C_1$–$C_4$-alkyl, unsubstituted phenyl or phenyl substituted by one to three substituents, each substituent being selected from the following: $C_1$–$C_4$-alkyl, $C_1$–$C_4$-alkoxy, OH, $C_1$–$C_4$-alkanoyloxy, benzyloxy, trifluoromethyl and halogen;

W is H, $C_1$–$C_4$-alkoxy, $C_1$–$C_4$-alkylthio, halogen, $C_1$–$C_4$-alkyl, or $C_1$–$C_4$-alkyl substituted by OH, $C_1$–$C_4$-alkoxy, CN, $COOR^{15}$ or $CONHR^{16}$;

$R^{15}$ is H or $C_1$–$C_4$-alkyl; and $R^{16}$ is H or $C_1$–$C_4$-alkyl;

wherein $R^1$ is optionally protected by a protecting group; comprising directly reacting a 2-aminopurine compound of formula II

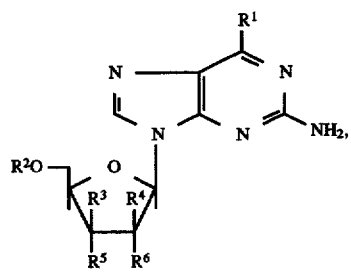

wherein $R^1$, $R^2$, $R^3$, $R^4$, $R^5$ and $R^6$ have the meanings indicated above, in HF/pyridine or HF/pyridine/$H_2O$ in the presence of a nitrite of formula III, $$R^{17}ONO \qquad (III),$$

wherein $R^{17}$ is tert-butyl, Li, Na or K;

optionally, if $R^2$ is hydrogen, converting $R^2$ to form 5'-phosphate; and optionally, if $R^1$ is protected, cleaving said protecting group; to obtain a 2-fluoropurine compound of formula I at a yield of at least 62.1%.

28. A process for production of a 2-fluoropurine compound of formula I

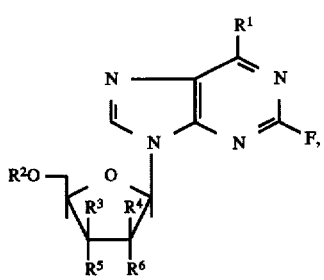

wherein $R^1$ is OH, $NH_2$, $NR^7R^8$ or $NR^9R^{10}$;

$R^2$ is hydrogen or

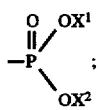

$X^1$ and $X^2$, independent of one another, are each H, Li, Na or K;

$R^3$, $R^4$, $R^5$ and $R^6$, independent of one another, are each H or OH, and $R^3$ and $R^5$ are not simultaneously both OH and $R^4$ and $R^6$ are not simultaneously both OH;

$R^7$ and $R^8$, independent of one another, are each H, $C_1$–$C_4$-alkyl, $C_7$–$C_8$-aralkyl, an unsubstituted heterocyclic radical, a heterocyclic radical substituted by F, Cl, Br, CN, OH, COOH, $C_1$–$C_4$-alkoxy or $C_1$–$C_4$-alkyl, unsubstituted $C_3$–$C_7$-cycloalkyl, $C_5$–$C_7$-cycloalkyl substituted by CN, OH, $C_1$–$C_4$-alkyl, methoxy, ethoxy, COOH, methoxycarbonyl, or ethoxycarbonyl, or $R^7$ and $R^8$ together with the N atom can form a $C_4$–$C_7$ ring, which optionally contains 1–3 additional heteroatoms, or, if $R^7$ is H, $R^8$ can also be OH or $NH_2$;

$R^9$ is H or $C_1$–$C_4$-alkyl;

$R^{10}$ is —$(CH_2)_n$—$R^{11}$,

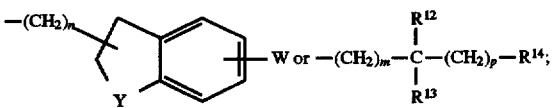

m, n and p, independent of one another, are each 0, 1 or 2;

$R^{11}$ is unsubstituted $C_3$–$C_7$-cycloalkyl, unsubstituted cyclohexenyl, unsubstituted bicycloheptyl, unsubstituted bicycloheptenyl, $C_5$–$C_7$-cycloalkyl substituted by $C_1$–$C_4$-alkyl, cyclohexenyl substituted by $C_1$–$C_4$-alkyl, bicycloheptyl substituted by $C_1$–$C_4$-alkyl or bicycloheptenyl substituted by $C_1$–$C_4$-alkyl;

Y is nitrogen, oxygen, sulfur, methylene, —$CH_2Z$— or —$ZCH_2$—; and

Z is nitrogen, oxygen or sulfur;

$R^{12}$ and $R^{13}$, independent of one another, are each H, OH, phenyl or $C_1$–$C_4$-alkyl;

$R^{14}$ is H, OH, $C_1$–$C_4$-alkyl, unsubstituted phenyl or phenyl substituted by one to three substituents, each substituent being selected from the following: $C_1$–$C_4$-alkyl, $C_1$–$C_4$-alkoxy, OH, $C_1$–$C_4$-alkanoyloxy, benzyloxy, trifluoromethyl and halogen;

W is H, $C_1$–$C_4$-alkoxy, $C_1$–$C_4$-alkylthio, halogen, $C_1$–$C_4$-alkyl, or $C_1$–$C_4$-alkyl substituted by OH, $C_1$–$C_4$-alkoxy, CN, $COOR^{15}$ or $CONHR^{16}$;

$R^{15}$ is H or $C_1$–$C_4$-alkyl; and
$R^{16}$ is H or $C_1$–$C_4$-alkyl;
comprising reacting a 2-aminopurine compound of formula II

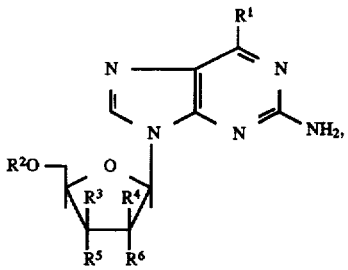

wherein $R^1$, $R^2$, $R^3$, $R^4$, $R^5$ and $R^6$ have the meanings indicated above, in HF/pyridine or HF/pyridine/$H_2O$ in the presence of a nitrite of formula III,

 $R^{17}ONO$           (III), wherein $R^{17}$ is tert-butyl, Li, Na or K;
and, optionally, if $R^2$ is hydrogen, converting $R^2$ to form 5'-phosphate.

29. A process according to claim 28, wherein $R^7$ and $R^8$ are each, independently, selected from the group consisting of $C_1$–$C_4$-alkyl, benzyl, phenethyl, 1-phenylethyl, 2-pyridyl, 3-pyridyl, 4-pyridyl, 2-furyl, 3-furyl, 2-thienyl, 3-thienyl, 2-pyrrolyl, 3-pyrrolyl, 2-indolyl, 3-indolyl, cyclopropyl, cyclobutyl, cyclopentyl, cyclohexyl or cycloheptyl.

30. A process according to claim 28, wherein $R^7$ and $R^8$ together are pyrrolidine, piperidine or morpholine.

31. A process according to claim 28, wherein $R^7$ and $R^8$ are each H.

32. A process according to claim 28, wherein $R^7$ and $R^8$ are each H, $C_1$–$C_4$-alkyl, $C_7$–$C_8$-aralkyl, unsubstituted $C_3$–$C_7$-cycloalkyl or $C_5$–$C_7$cycloalkyl substituted by CN, OH, $C_1$–$C_4$-alkyl, methoxy, ethoxy, COOH, methoxycarbonyl or ethoxycarbonyl.

33. A process according to claim 28, wherein $R^7$ and $R^8$ are each H, $C_1$–$C_4$-alkyl, $C_7$–$C_8$-aralkyl, unsubstituted $C_3$–$C_7$-cycloalkyl or $C_5$–$C_7$-cycloalkyl substituted by CN, OH, $C_1$–$C_4$-alkyl, methoxy, ethoxy, COOH, methoxycarbonyl or ethoxycarbonyl, 2-pyridyl, 3-pyridyl, 4-pyridyl, 2-furyl, 3-furyl, 2-thienyl, 3-thienyl, 2-pyrrolyl, 3-pyrrolyl, 2-indolyl or 3-indolyl, or $R^7$ and $R^8$ together with the N atom are pyrrolidine, piperidine or morpholine.

34. A process according to claim 28, wherein $R^7$ and $R^8$, independent of one another, are each H, $C_1$–$C_4$-alkyl, $C_7$–$C_8$-aralkyl, an unsubstituted heterocyclic radical containing 5–10 ring atoms with 1–3 hetero ring atoms each selected from N, O and S atoms, a heterocyclic radical containing 5–10 ring atoms with 1–3 hetero ring atoms each selected from N, O and S atoms substituted by F, Cl, Br, CN, OH, COOH, $C_1$–$C_4$-alkoxy, $C_1$–$C_4$-alkyl, unsubstituted $C_3$–$C_7$-cycloalkyl, $C_5$–$C_7$-cycloalkyl substituted by CN, OH, $C_1$–$C_4$-alkyl, methoxy, ethoxy, COOH, methoxycarbonyl, or ethoxycarbonyl, or $R^7$ and $R^8$ together with the N atom can form a $C_4$–$C_7$ ring, which optionally contains 1–3 hetero ring atoms each selected from N and O atoms, or, if $R^7$ is H, $R^8$ can also be OH or $NH_2$.

35. A process according to claim 34, wherein $R^{17}$ is Li, Na, or K.

36. A process according to claim 35, wherein $R^{17}$ is K.

37. A process according to claim 35, wherein $R^{17}$ is Na.

38. A process according to claim 34, wherein said compound of formula II is reacted in HF/pyridine.

39. A process according to claim 38, wherein said HF/pyridine contains 10–60% HF.

40. A process according to claim 38, wherein said compound of formula II is reacted in 40–60% HF/pyridine.

41. A process according to claim 38, further comprising instilling the HF/pyridine reaction mixture in a suspension of calcium carbonate and ice water followed by removal of undissolved precipitate by filtration and evaporation of the resultant filtrate.

42. A process according to claim 34, wherein two of the groups $R^3$, $R^4$, $R^5$ and $R^6$ are not OH and the remaining two groups are H.

43. A process according to claim 42, wherein $R^5$ and $R^6$ are OH.

44. A process according to claim 42, wherein $R^5$ and $R^5$ are OH.

45. A process according to claim 34, wherein said compound of formula II is reacted in HF/pyridine/$H_2O$ containing up to 10% $H_2O$.

46. A process according to claim 34, wherein the reaction of a compound of formula II is conducted at −50° C.–+25° C.

47. A process according to claim 34, wherein said nitrite of formula III is tert-butylnitrite or sodium nitrite.

48. A process according to claim 34, wherein said compound of formula II is 2-aminoadenosine.

49. A process according to claim 34, wherein said compound of formula II is 2-amino-6-piperidino-adenosine.

50. A process according to claim 34, wherein said compound of formula I is 2-fluoroadenosine, 2-fluoro-6-piperidino-adenosine or 2-fluorinosine.

51. A process according to claim 34, wherein $R^2$ is H.

52. A process according to claim 34, wherein $X^1$ and $X^2$ are each H.

* * * * *